US005981299A

United States Patent [19]
Lance, III et al.

[11] Patent Number: 5,981,299
[45] Date of Patent: Nov. 9, 1999

[54] MAMMALIAN PANCREATIC CHOLESTEROL ESTERASE

[75] Inventors: Louis George Lance, III, St. Louis; Curtis A. Spilburg, Chesterfield, both of Mo.

[73] Assignee: CV Therapeutics, Inc., Palo Alto, Calif.

[21] Appl. No.: 09/123,960

[22] Filed: Jul. 29, 1998

Related U.S. Application Data

[62] Division of application No. 08/461,881, Jun. 5, 1995, Pat. No. 5,792,832, which is a division of application No. 08/305,501, Sep. 13, 1994, Pat. No. 5,437,111, which is a continuation of application No. 07/856,910, May 12, 1992, abandoned, which is a continuation of application No. 07/434,899, Nov. 13, 1989, Pat. No. 5,173,408.

[51] Int. Cl.$^6$ .................................................. G01N 33/53
[52] U.S. Cl. .......................... 436/547; 435/7.1; 435/183; 435/196; 424/146.1; 424/178.1; 436/548; 530/413; 530/810
[58] Field of Search .............................. 435/7.1, 19, 174, 435/183, 196; 436/547, 548; 530/413, 810; 426/146.1, 178.1

[56] References Cited

U.S. PATENT DOCUMENTS

| | | |
|---|---|---|
| 4,732,757 | 3/1988 | Stolle et al. . |
| 4,944,944 | 7/1990 | Tang et al. . |
| 5,017,565 | 5/1991 | Lange et al. . |
| 5,063,210 | 11/1991 | Lange et al. . |
| 5,173,408 | 12/1992 | Lange et al. . |
| 5,200,183 | 4/1993 | Tang et al. . |
| 5,210,183 | 5/1993 | Lindahl et al. . |
| 5,352,601 | 10/1994 | Lange et al. . |
| 5,432,058 | 7/1995 | Lange et al. . |

FOREIGN PATENT DOCUMENTS

WO 90/12579  11/1990  WIPO .

OTHER PUBLICATIONS

Kyger et al., *Biochemical and Biophysical Research Communications*, vol. 164:3, pp. 1302–1309, Cloning of the Bovine Pancreatic Cholesterol Esterase/Lysophospholipase, (1989).

Custer et al., *Am. J. Physiol.*, vol. 266, pp. F767–F774, Expression of Na–$P_i$ cotransport in rat kidney; localization by RT–PCR and immunohistochemistry, (1994).

Bosner et al., *Proc. Natl. Acad. Sci. USA*, vol. 85, pp. 438–7442, Receptor–like function of heparin in the binding and uptake of neutral lipids, (1988).

Vahouny et al. *Proc. J. Exp. Biol. Med.*, vol. 116, p. 496, Absolute Requirement for Free Sterol for Absorption by Rat Intestinal Mucosa, (1964).

Casdorph, *Cholestyramine and Ion–Exchange Resins*, pp. 211–256.

Wagner, *Nature*, vol. 372, pp. 333–335, Gene inhibition using antisene oligodeoxynucleotides, (1994).

Ullrich et al., *The EMBO Journal*, vol. 3(2), pp. 3621–3624, Isolation of the human insulin–like growth factor I gene using a single synthetic DNA probe, (1984).

Werner et al., *J. Biol. Chem.* vol. 269, pp. 6637–6639, Increase of Na/$P_i$–contransport Encoding mRNA in Response to Low $P_i$ Diet in Rat Kidney Cortex, (1994).

Abouakil et al., *Biochemica et Biophysica Acta.*, vol. 961, pp. 299–308, Purification of pancreatic carboxylic–ester hydrolase by immunoaffinity and its application to the human bile–salt–stimulated lipase, (1988).

Han et al., *Biochemistry*, vol. 26, pp. 1617–1625, Isolation of Full–Length Putative Rat Lysophospholipase cDNA using Improved Methods for mRNA Isolation and cDNA Cloning (1987).

Stoll et al., *Biochem. J.*, vol. 180, pp. 465–470, Effect of Dietary Phosphate Intake on Phosphate Transport by Isolated Rat Rental Brush–Border Vesicles, (1979).

Labow et al., *Arch. Biochem. Biophys. Acta*, vol. 749, pp. 32–41, Porcine Cholesterol Esterase, a Multiform Enzyme, (1975).

Brown et al., *Biochem Biophys. Acta*, vol. 769, pp. 471–478, Sodium–Dependent Phosphate Trnasport by Apical Membrane Vesicles From a Cultured Renal Epithelial Cell Line (LLC–$PK_1$), (1984).

Rudd et al., *Biochemica et Biophysica Acta*, vol. 918, pp. 106–114, Isolation of two forms of carboxylester lipase (cholestero esterase) from porcine pancrease, (1987).

Jaye et al., *Nucleic Acids Research*, vol. 11(8), pp. 2325–2335, Isolation of a human anit–haemophilic factor IX cDNA clone using a unique 52–base synthetic oligonucleotide probe deduced from the amino acid sequence of bovine factor IX, (1983).

Cossum et al., *J. Pharmacol. Exper. Therapeutics*, vol. 267, pp. 1181–1190, Disposition of the $^{14}$C–Labeled Phosphorothioate Oligonucleotide ISIS 2105 after Intravenous Administration to Rats, (1993).

Fitzpatrick et al., *Journal of Virology*, vol. 62(11), pp. 4239–4248, Expression of Bovine Herpesvirus 1 Glycoproteins gI and GIII in Transfected Murine Cells, (1988).

Cohen, *Advances in Pharmacology*, vol. 25, pp. 319–339, Gene–Mimetic Substances: Drugs Designed to Intervene in Gene Expression, (1994).

(List continued on next page.)

*Primary Examiner*—Laurie Scheiner
*Attorney, Agent, or Firm*—McDonnell, Boehnen, Hulbert & Berghoff

[57] ABSTRACT

The invention provides methods for the purification to homogeneity of pancreatic cholesterol esterase in useful quantities from a variety of mammalian species. The gene for a mammalian pancreatic cholesterol esterase has been cloned and sequenced, and is useful for expressing cholesterol esterase in a transformed eukaryotic or prokaryotic cell culture. Thus, methods according to the invention enable the production of large quantities of pancreatic cholesterol esterase for the screening of inhibitors, the production of antibodies, and for commercial purposes related to the alteration of cholesterol/cholesterol ester composition of materials containing free or esterified cholesterol.

2 Claims, 7 Drawing Sheets

OTHER PUBLICATIONS

Tenehouse et al., *J. Clin. Invest.*, vol. 93, pp. 671–676, Renal Na+–Phosphate Cotransport in Murine X–linked Hypophosphatemic Rickets, (1994).

Gao et al., *Molec. Pharacol.*, vol. 43, pp. 45–50, Cellular Pharmacology of Phosphorothioate Homooligodeoxynucleotides in Human Cells, (1993).

Emtage et al., *Proc. Natl. Acad. Sci. USA*, vol. 80, pp. 3671–3675, Synthesis of calf prochymosin (prorennin) in *Escherichia coli*, (1983).

Dean et al., *Proc. Natl. Acad. Sci. USA*, vol. 91, pp. 11762–11766, Inhibition of protein kinase C–α expression in mice after systemic administration of phosphorothioate antisense oligodeoxynucleotides, (1994).

Leonetti et al., *Proc. Natl. Acad. Sci. USA*, vol. 88, pp. 2702–2706, Intracellular distribution of microinjected antisense oligonucleotides, (1991).

Yakubov et al., *Proc. Natl. Acad. Sci. USA*, vol. 86, pp. 6454–6458, Mechanism of oligonucleotide uptake by cells: Involvement of specific receptors, (1989).

Zamecnik et al., *Proc. Natl. Acad. Sci. USA*, vol. 91, pp. 3156–3160, Electron micrographic studies of transport of oligodeoxynucleotides across eukaryotic cell membranes, (1994).

Magagnin et al., *Proc Natl. Acad. Sci. USA*, vol. 90, pp. 5979–5983, Expression clofing of human and rat renal cortex Na/$P_i$ cotransport, (1993).

Agrawal et al., *Proc. Natl. Acad. Sci. USA*, vol. 88, pp. 7595–7599, Pharmacokinetics, biodistribution, and stability of oligodeoxynucleotide phosphorothioates in mice, (1991).

Morishita et al., *Proc. Natl. Acad. Sci. USA*, vol. 90, pp. 8474–8478, Single intraluminal delivery of antisene cdc2 kinase and proliferating–cell nuclear antigen oligonucleotides results in chronic inhibition of neointimal hyperplasia, (1993).

Ratajczak et al., *Proc. Natl. Acad. Sci. USA*, vol. 89, pp. 11823–11827, In vivo treatment of human leukemia in a scid mouse modelwith c–myb antisene oligeoxynucleotides, (1992).

Towbin et al., *Proc. Natl. Acad. Sci. USA*, vol. 76, pp. 4350–4354, Electrophoretic transfer of proteins from polyacrylamide gels to nitrocellulose sheets: Procedural and some applications, (1979).

Stein et al., *Science*, vol. 261, pp. 1004–1012, Antisene Oligonucleotides as Therapeutic Agents—Is the Bullet Really Magical, (1993).

Laemmli, U.K., *Nature*, vol. 227, pp. 680–685, Cleavage of Structural Proteins during the Assembly of the Head of Bacteriophage T4, (1970).

Simons, et al., *Nature*, 359: 67–70, Antisene c–myb oligonucleotides inhibit intimal arterial smooth muscle cell accumulation in vivo, (1992).

Allain et al., *Clin. Chem.*, vol. 20, pp. 470–475, Enzymatic Determination of Total Serum Cholestrol, (1974).

Neckers et al., *Am. J. Physiol*, vol. 265, pp. L1–L12, Antisene techology: biological utility and practical considerations (1993).

FIG. 1

```
          10          20          30          40          50
           *           *           *           *           *
     LGASRLGPSP  GCLAVASAAK  LGSVYTEGGF  VEGVNKKLSL  FGDSVDIFKG
          60          70          80          90         100
           *           *           *           *           *
     IPFAAAPKAL  EKPERHPGWQ  GTLKAKSFKK  RCLQATLTQD  STYGNEDCLY
         110         120         130         140         150
           *           *           *           *           *
     LNIWVPQGRK  EVSHDLPVMI  WIYGGAFLMG  ASQGANFLSN  YLYDGEEIAT
         160         170         180         190         200
           *           *           *           *           *
     RGNVIVVTFN  YRVGPLGFLS  TGDSNLPGNY  GLWDQHMAIA  WVKRNIEAFG
         210         220         230         240         250
           *           *           *           *           *
     GDPDNITLFG  ESAGGASVSL  QTLSPYNKGL  IKRAISQSCV  GLCPWAIQQD
         260         270         280         290         300
           *           *           *           *           *
     PLFWAKRIAE  KVGCPVDDTS  KMAGCLKITD  PRALTLAYKL  PLGSTEYPKL
         310         320         330         340         350
           *           *           *           *           *
     HYLSFVPVID  GDFIPDDPVN  LYANAADVDY  IAGTNDMDGH  LFVGMDVPAI
         360         370         380         390         400
           *           *           *           *           *
     NSNKQDVTEE  DFYKLVSGLT  VTKGLRGANA  TYEVYTEPWA  QDSSQETRKK
         410         420         430         440         450
           *           *           *           *           *
     TMVDLETDIL  FLIPTKIAVA  QHKSHAKSAN  TYTYLFSQPS  RMPIYPKWMG
         460         470         480         490         500
           *           *           *           *           *
     ADHADDLQYV  FGKPFATPLG  YRAQDRTVSK  AMIAYWTNFA  RTGDPNTGHS
         510         520         530         540         550
           *           *           *           *           *
     YVPANWDPYT  LEDDNYLEIN  KQMDSNSMKL  HLRTNYLQFW  TQTYQALPTV
         560         570         580         590
           *           *           *           *
     TSAGASLLPP  EDNSQASPVP  PADNSGAPTE  PSAGDSEVAQ  MPVVIGF
```

FIG. 2a

```
                              10         20
                    GCCTAGAGGC AGACACTCAC TATGGGGCG

*   10    *    20    *    30    *    40    *    50
        GCTGGGAGCT AGCCGTCTTG GGCCGTCGCC TGGCTGCTTG GCAGTAGCGA
          30          40          50          60          70
        cCTGGAgGtT CTGTTTCT-T GGC-cTCACC -TGCTGCTTG GCAGcTGCTT

*   60    *    70    *    80    *    90    *   100
        GTGCAGCGAA GTTGGGCTCC GTATACACCG AAGGCGGCTT CGTGGAGGGC
          80          90         100         110         120
        GTGCTGCAAA GTTGGGTGCT cTGTACACAG AAGGCGGTTT TGTGGAGGGC

*  110    *   120    *   130    *   140    *   150
        GTCAACAAGA AGCTGAGCCT CTTTGGCGAC TCTGTTGACA TCTTCAAGGG
                                   TGG
         130         140          :      160         170         180
        GTCAACAAGA AACTcAGTCT CTGTGGTGAC TCTGTTGACA TCTTCAAGGG

*  160    *   170    *   180    *   190    *   200
        CATCCCCTTC GCTGCCGCCC CCAAGGCCCT GGAGAAGCCC GAGCGACACC
          190         200         210         220
        CATCCCCTTC GCTACC---G CCAAGACCCT GGAGAATCCt cAGCGtCACC

*  210    *   220    *   230    *   240    *   250
        CCGGCTGGCA AGGGACCCTG AAGGCCAAGA GCTTTAAGAA ACGGTGCCTG
                                       A
          230         240         250 .       260         270
        CTGGCTGGCA AGGGACACTG AAGGCtCAG- ACTTcAAGAA ACGATGTCTA

*  260    *   270    *   280    *   290    *   300
        CAGGCCACGC TCACGCAGGA CAGCACCTAC GGAAATGAAG ACTGCCTCTA
          280         290         300         310         320
        CAAGCCACCa TCACcCAGGA TGATACCTAT GGgCAAGAAG ACTGCCTCTA

*  310    *   320    *   330    *   340    *   350
        CCTCAACATC TGGGTCCCCC AGGGCAGGAA GGAAGTCTCC CACGACCTGC
          330         340         350         360         370
        TCTCAACATC TGGGTCCCtC AGGGCAGGAA GcAAGTGTCT CATGACCTGC
```

FIG. 2b

```
        360        370        380        390        400
    *    *     *    *     *    *     *    *     *    *
CCGTCATGAT CTGGATCTAT GGAGGCGCCT TCCTCATGGG GGCCAGCCAA
   380        390        400        410        420
CTGTGATGGT CTGGATCTAT GGAGGTGCCT TCCTCATGGG GTCTGGCCAG 410        420        430        440        450
    *    *     *    *     *    *     *    *     *    *
GGGGCCAACT TTCTCAGCAA CTACCTCTAC GACGGGGAGG AGATTGCCAC
   430        440        450        460        470
GGAGCCAATT TTCTCAAGAA TTACCTGTAT GATGGGGAAG AGATCGCCAC 460        470        480        490        500
    *    *     *    *     *    *     *    *     *    *
ACGGGGCAAC GTCATCGTGG TCACGTTCAA CTACCGCGTT GGGCCCCTGG
   480        490        500        510        520
TAGAGCCAAT GTCATTGTGG TCACCTTCAA CTACCGTGTC GGACCCTTGG 510        520        530        540        550
    *    *     *    *     *    *     *    *     *    *
GCTTTCTCAG CACCGGGGAC TCCAACCTGC CAGGTAACTA TGGCCTTTGG
   530        540        550        560        570
GTTTCCTTAG CACCGGAGAT GCTAACCTTC CAGGTAACTT TGGACTTCGA 560        570        580        590        600
    *    *     *    *     *    *     *    *     *    *
GATCAGCACA TGGCCATTGC TTGGGTGAAG AGGAACATTG AGGCCTTCGG
   580        590        600        610        620
GATCAGCACA TGGCTATTGC CTGGGTGAAG AGGAACATTG CAGCCTTTGG 610        620        630        640        650
    *    *     *    *     *    *     *    *     *    *
AGGAGACCCC GACAACATCA CCCTCTTTGG GGAGTCGGCC GGAGGCGCCA
   630        640        650        660        670
AGGAGACCCC GATAACATCA CCATCTTTGG GGAATCTGCT GGAGGTGCCA 660        670        680        690        700
    *    *     *    *     *    *     *    *     *    *
GCGTCTCTCT GCAGACCCTC TCTCCCTACA ACAAGGGCCT CATCAAGCGA
```

FIG. 2c

```
      680        690        700        710        720
 TTGTCTCTCT GCAGACCCTC TCCCCATACA ACAAGGGCCT CATCCGGCGA

* 710      * 720      * 730      * 740      * 750
 GCCATCAGCC AGAGTGGAGT GGGTTTGTGC CCTTGGGCCA TCCAGCAGGA 730        740        750        760        770
 GCCATCAGTC AGAGTGGTGT GGCACTGAGC CCCTGGGCCA TCCAGGAGAA

* 760      * 770      * 780      * 790      * 800
 CCCCCTCTTC TGGGCTAAAA GGATTGCAGA GAAGGTGGGC TGCCCCGTGG 780        790        800        810        820
 TCCACTTTTC TGGGCCAAAA CGATCGCTAA GAAGGTGGGA TGCCCCACAG

* 810      * 820      * 830      * 840      * 850
 ACGACACCAG CAAGATGGCT GGGTGTCTGA AGATCACTGA .CCCCCGTGCC 830        840        850        860        870
 ATGATACCGC CAAGATGGCT GGGTGTCTGA AGATCACAGA TCCCCGAGCC

* 860      * 870      * 880      * 890      * 900
 CTGACGCTGG CCTATAAGCT GCCCCTGGGA AGCACGGAAT ACCCCAAGCT 880        890        900        910        920
 TTGACACTGG CCTACAGGTT GCCCTTGAAA AGCCAGGAGT ACCCCATTGT

* 910      * 920      * 930      * 940      * 950
 GCACTATCTG TCCTTCGTCC CCGTCATCGA TGGAGACTTC ATCCCTGATG 930        940        950        960        970
 GCACTACCTG GCCTTCATCC CTGTCGTCGA TGGTGACTTC ATTCCTGATG

* 960      * 970      * 980      * 990      * 1000
 ACCCCGTCAA CCTGTACGCC AACGCCGCGG ACGTCGACTA CATAGCGGGC 980        990       1000       1010       1020
 ATCCCATCAA CCTGTACGAC AACGCTGCTG ACATTGACTA CTTAGCGGGT
```

FIG. 2d

```
        *  1010       *  1020       *  1030       *  1040       *  1050
        *      *      *      *      *      *      *      *      *      *
     ACCAATGACA   TGGACGGCCA   CCTCTTTGTC   GGGATGGACG   TGCCAGCCAT
     1030         1040         1050         1060         1070
     AtTAATGACA   TGGAtGGCCA   CCTgTTTGcT   AcAgTTGACG   TGCCcGCCAT

*  1060       *  1070       *  1080       *  1090       *  1100
        *      *      *      *      *      *      *      *      *      *
     CAACAGCAAC   AAACAGGACG   TCACGGAGGA   GGACTTCTAT   AAGCTGGTCA
     1080         1090         1100         1110         1120
     CgACAAggcC   AAgCAGGAtG   TCACaGAGGA   GGACTTCTAc   AgGCTaGTCA

*  1110       *  1120       *  1130       *  1140       *  1150
        *      *      *      *      *      *      *      *      *      *
     GCGGGCTCAC   CGTCACCAAG   GGGCTCAGAG   GTGCCAATGC   CACGTACGAG
     1130         1140         1150         1160         1170
     GtGGaCaCAC   TGTCgCCAAG   GGGCTtAaAG   GcaCCcAaGC   CACcTtTGAc

*  1160       *  1170       *  1180       *  1190       *  1200
        *      *      *      *      *      *      *      *      *      *
     GTGTACACCG   AGCCCTGGGC   CCAGGACTCA   TCCCAGGAGA   CCAGGAAGAA
     1180         1190         1200         1210         1220
     AtCTACACTg   AGTCCTGGGC   CCAGGACcCg   TCCCAGGAGA   aCAtGAAGAA

*  1210       *  1220       *  1230       *  1240       *  1250
        *      *      *      *      *      *      *      *      *      *
     GACCATGGTG   GACCTGGAGA   CTGACATCCT   CTTCCTGATC   CCCACAAAGA
     1230         1240         1250         1260         1270
     GACAgTGGTG   GcCTTtGAGA   CTGACATaCT   CTTCCTGATC   CCCACAgAGA

*  1260       *  1270       *  1280       *  1290       *  1300
        *      *      *      *      *      *      *      *      *      *
     TTGCCGTGGC   CCAGCACAAG   AGCCACGCCA   AGAGCGCCAA   CACCTACACC
                                      G
     1280         1290         :            1310         1320
     TgGCtcTGGC   CCAGCA-cAG   AcCCAtGCCA   AGAGtGCCAA   gACCTACtCt

*  1310       *  1320       *  1330       *  1340       *  1350
        *      *      *      *      *      *      *      *      *      *
     TACCTGTTCT   CCCAACCGTC   TCGGATGCCC   ATCTACCCCA   AGTGGATGGG
```

FIG. 2e

```
1330       1340       1350       1360       1370
TACCTGTTtT CCCAcCCtTC ACGAATGCCt ATCTACCCAa AATGGATGGG

* 1360    * 1370    * 1380    * 1390    * 1400
GGCTGACCAC GCCGATGACC TCCAGTATGT CTTCGGGAAG CCCTTCGCCA 1380       1390       1400       1410       1420
GGCAGACCAC GCTGATGACC TCCAGTAcGT CTTTGGGAAG CCCTTtGCCA

* 1410    * 1420    * 1430    * 1440    * 1450
CCCCCCTGGG CTACCGGGCC CAAGACAGGA CTGTCTCCAA GGCCATGATT 1430       1440       1450       1460       1470
CCCCACTGGG CTACCGGGCC CAAGACAGGA CTGTCTCCAA GGCCATGATT

* 1460    * 1470    * 1480    * 1490    * 1500
GCCTACTGGA CCAACTTTGC CAGAACTGGG GACCCTAACA CGGGCCACTC 1480       1490       1500       1510       1520
GCCTACTGGA CCAACTTTGC CAaGAgTGGG GACCCcAACA TGGGCAACTC

* 1510    * 1520    * 1530    * 1540    * 1550
GACAGTGCCC GCAAACTGGG ATCCCTACAC CCTGGAAGAT GACAACTACC 1530       1540       1550       1560       1570
AcCcGTGCCC ACAcACTGGt AcCCtTAtAC CAtGGAgAAT GgTAACTACC

* 1560    * 1570    * 1580    * 1590    * 1600
TGGAAATCAA CAAGCAGATG GACAGCAACT CTATGAAGCT GCATCTGAGG 1580       1590       1600       1610       1620
TGGAcATCAA tAAGaAaATa AcCAGCAcCT CcATGAAGGa GCAcCTAAGG

* 1610    * 1620    * 1630    * 1640    * 1650
ACCAACTACC TGCAGTTCTG GACCCAGACC TACCAGGCCC TGCCCACGGT 1630       1640       1650       1660       1670
GAAAAgTtCC TcAAGTTCTG GgCtGTGACA TTCGAGATgC TGCCCACtGT
```

FIG. 2f

```
        1660       1670       1680       1690       1700
         *          *          *          *          *
    GACCAGCGCG GGGGCCAGCC TGCTGCCCCC CGAGGACAAC TCTCAGGCCA
        1680       1690         1700       1710
    ----G-GTTG GTGACCACAC -T---CCCCC TGAGGATGAC TCAGAGGCTG 1710       1720       1730       1740       1750
         *          *          *          *          *
    GCCCCGTGCC CCCAGCGGAC AACTCCGGGG CTCCCACCGA ACCCTCTGCG
      1720       1730       1740       1750       1760
    CCCCCGTCCC ACCTACAGAC GACTCCCAGG GTGGTCCTGT CCCACCTACA 1760       1770       1780       1790       1800
         *          *          *          *          *
    GGTGACTCTG AGGTGGCTCA GATGCCTGTC GTCATTGGTT TCTAATGTCC
      1770       1780       1790       1800       1810
    GATGACTCTC AGACAACACC GGTGC-CCCC AACAGACAAC TCTC-AGGCT 1810       1820       1830       1840       1850
         *          *          *          *          *
    TTGGCCTCCA GGGGCCACAG GAGACCCCAG GGCCCACTTC CCTCCCAAGT
      1820       1830       1840       1850       1860
    GGTGAC-TCT GTGGAGG-CT CAGATGCCTG GTCCCATTGG CTTCTAAAG- 1860       1870        *
         *          *
    GCCTCCTGAA TAAAGCCTCA ACCATCTC(POLY A)
       1870
    TCC-TATAAA CCGGGGC
```

MAMMALIAN PANCREATIC CHOLESTEROL ESTERASE

This application is a divisional of application Ser. No. 08/461,881, filed Jun. 5, 1995, now U.S. Pat. No. 5,792,832, which is a divisional of application Ser. No. 08/305,501, filed Sep. 13, 1994, now U.S. Pat. No. 5,437,111, which is a continuation of application Ser. No. 07/856,910, filed May 12, 1992, now abandoned, which is a continuation of application Ser. No. 07/434,899, filed Nov. 13, 1989, now U.S. Pat. No. 5,173,408.

BACKGROUND OF THE INVENTION

1. Field of the Invention

The invention relates to enzymes involved in the metabolism of cholesterol and more specifically to the cholesterol esterase secreted by the pancreas in mammals. Cholesterol metabolism is of critical interest to those involved in protecting human health. Atherosclerosis is the leading cause of death in the United States and reduction of serum cholesterol levels has recently been embraced as a national health priority. See NIH Consensus Panel Report, J.A.M.A. 253: 2094 (1985). NIH recommendations include measurement of serum cholesterol in all adults, with efforts to reduce cholesterol in those individuals with levels above 200 mg %. In this regard front line therapy is a reduction in the amount of cholesterol and triglycerides ingested, followed by the use of agents that interfere with absorption of ingested lipids. See Consensus Full Report, Arch. Inst. Med. 148: 36 (1988).

Pancreatic cholesterol esterase plays a pivotal role in the absorption of cholesterol and fatty acids. The inhibition of cholesterol esterase could lead to reduced serum cholesterol levels. Numerous approaches to developing inhibitors of cholesterol esterase will likely be attempted, including the use of chemical inhibitors. Therapeutic biologicals, such as monoclonal or polyclonal antibodies to pancreatic cholesterol esterase have great potential. In particular, antibodies against purified cholesterol esterase can be isolated from the milk of immunized cows and used as an ingestible therapeutic. Analogs of pancreatic cholesterol esterase are proteins similar to cholesterol esterase, but with sufficient variation in amino acid sequence to bind cholesterol asters without releasing free cholesterol and fatty acids. If such analogs can be developed they will serve as powerful inhibitors of cholesterol esterase function.

Whatever type of inhibitor is being developed, large quantities of highly purified enzyme are required to test the efficacy of any potential inhibitor, as well as to better understand the enzyme and thus allow the development of further therapeutic means. There is, therefore, a need for methods to purify useful quantities of homogeneous pancreatic cholesterol esterase. In addition, for the preparation of analog inhibitors, the amino acid sequence of the enzyme and its underlying DNA sequence must be known. Thus, there is a need for a cloned DNA sequence encoding cholesterol esterase, from which the DNA and amino acid sequences may be determined.

Finally, pancreatic cholesterol esterase has considerable commercial utility for enzymatic hydrolysis or synthesis of ester linkages in the preparation of biologicals or foodstuffs such as dairy products. There is, therefore, a need for a means of producing commercially significant, large-scale quantities of homogeneous cholesterol esterase, especially from cows, which cannot be met by purification of the enzyme from natural sources. What is needed, then, is a means for producing pancreatic cholesterol esterase through the use of recombinant DNA expression vectors in a suitable host cell or organism, as well as a means of large-scale purification of the enzyme so expressed.

2 Information Disclosure

Borja et al., 1964, Proc. J. Exp. Biol. and Med. 116: 496, teach that cholesterol esterase is secreted by the pancreas, and chat its catalysis of cholesterol ester hydrolysis to produce free cholesterol and free fatty acids is essential for the absorption of cholesterol. Bosner et al., 1988, Proc. Natl. Acad. Sci. USA 85: 7438, teach that cholesterol esterase performs its function while anchored to the intestinal membrane via a receptor-like interaction with brush border membrane associated heparin. Lange and Spilburg in U.S. Pat. No. 5,017,565, teach sulfated polysaccharide inhibitors of human pancreatic cholesterol esterase which are effective in blocking the absorption of cholesterol and fatty acids into intestinal calls.

Numerous procedures for the preparation of pancreatic cholesterol esterase have been reported. See, e.g., Allain et al., 1974, Clin. Chem. 20: 470, Calme et al., 1975, Arch. Biochem. Byophys. 168: 57, Labow et al., 1983, Biochem. Byophys. Acta 749: 32. In general, the reported procedures are tedious and give poor yields of heterogeneous material. Production of significant quantities of homogeneous material has not been achieved. For example, the commercially available cholesterol esterase, prepared by the method of Allain et al., is less than 5% pure according to both physical and functional assays. None of the existing preparative procedures has been useful for purifying cholesterol esterase from several different mammalian species.

BRIEF SUMMARY OF THE INVENTION

The present invention is directed toward the preparation of useful quantities of homogeneous mammalian pancreatic cholesterol esterase. The invention encompasses methods for large-scale purification of pancreatic cholesterol esterase from natural sources or from prokaryotic or eukaryotic cell cultures producing recombinant mammalian pancreatic cholesterol esterase. The invention also comprises mammalian pancreatic cholesterol esterases purified according to such methods, and the use of such purified enzymes to produce and purify antibodies to such enzymes, and to screen potential inhibitors to such enzymes. In addition, the invention comprises the use of such purified enzyme to alter the cholesterol composition of food-stuffs and biologics.

The invention further comprises cloned DNA sequences encoding mammalian pancreatic cholesterol esterase, expression vectors containing such DNA sequences, and prokaryotic or eukaryotic cell cultures harboring said expression vectors whereby said cell cultures are capable of producing mammalian pancreatic cholesterol esterase. The invention additionally comprises a process for commercial-scale production and purification of mammalian pancreatic cholesterol esterase through the application of the aforementioned purification methods to the supernatants of said mammalian pancreatic cholesterol esterase-producing call cultures. The invention finally comprises homogeneous mammalian pancreatic cholesterol esterase produced by such a process.

BRIEF DESCRIPTION OF THE DRAWINGS

FIG. 1. The deduced amino acid sequence of bovine pancreatic cholesterol esterase.

FIGS. 2A–25. The cDNA sequence of bovine pancreatic cholesterol esterase. The underlined region of the cholesterol esterase cDNA is the complementary sequence of the oligonucleotide probe.

DETAILED DESCRIPTION OF THE INVENTION

Large-scale purification to homogeneity of mammalian pancreatic cholesterol esterase from human, bovine, porcine, and rat pancreas has now been achieved through the use of sulfated matrices in affinity chromatography. This is the first method ever to allow purification of this enzyme from all mammalian species tested. The major form of the enzyme purified from bovine pancreas has a molecular weight of 72 kilodaltons (kDa) and has never before been detected.

The observation that certain sulfated polysaccharides can decrease cholesterol absorption was recently disclosed in copending U.S. Pat. No. 5,017,565, which is incorporated herein by reference. The sulfated polysaccharides reported in that investigation have the characteristic of binding to mammalian pancreatic cholesterol esterase. Thus, it is possible to use these compounds as an affinity matrix for the purification of pancreatic cholesterol esterase. Pancreatic cholesterol esterase contains a specific sulfate recognition site which allows it to bind to a large number of sulfated compounds which include, but are not limited to, heparin-agarose, Mono S, SP-Sephadex, cellulose sulfate, pectin sulfate, chitin sulfate, chitosan sulfate and 2, 3' or 6-congeners of chitosan sulfate, agar sulfate, amylopectin sulfate and any combination of monomers or polymers of the above. Those skilled in the art will recognize that other polysaccharides or resins may become sulfated through the action of chlorosulfate, sulfur dioxide, or other sulfating agents, whereby, in view of the above, such sulfated polysaccharides or resins could be employed as affinity matrices for the purification of pancreatic cholesterol esterase. Preferably, sulfated polysaccharides are used as the affinity matrix. In particular, sulfated cellulose which has been sulfated to an extent insufficient to make it soluble in water or heparin agarose are most preferred.

The binding of sulfated polysaccharides by pancreatic cholesterol esterase involves one or more specific regions of the protein, one of which in the bovine protein is represented by the amino acid sequence MDGHLFATVDVPAID-KAKQDV. Those skilled in the art will recognize that the sulfate binding sites of the human, porcine, and rat pancreatic cholesterol esterase enzymes, and of mammalian pancreatic cholesterol esterase enzymes will have substantially the same amino acid sequence. Substantially the same amino acid sequence is understood to mean an amino acid sequence in which any amino acid substitutions are conservative and do not significantly affect the function of the protein or any domain or region thereof (e.g., the ability of the region described above to bind to sulfated polysaccharides).

Specific amino acid sequences that bind sulfated agents have been identified by chemical cross-linking between the amino acid sequence and the sulfated agent, followed by cleavage of the protein to obtain the sulfated agent-bound oligopeptide and determination of the amino acid sequence of the oligopeptide. An oligopeptide having the amino acid sequence KKRCLQ has been identified as a binding site for sulfated agents on bovine rat and human cholesterol esterase. Binding of sulfated agents to this site on the enzyme does not inhibit enzyme function. In contrast, the oligopeptide PAINKGNKKV from human pancreatic cholesterol esterase binds sulfated agents in a manner that inhibits enzyme function. This binding site is only partially formed in the rat and bovine cholesterol esterases and comprises, respectively, the amino acid sequence PAID-KAKQDV or PAINSNKQDV. The inhibitory binding sequence is encoded in the human gene by the nucleotide sequence CCTGCCATCAACAAGGGCAACAA-GAAAGTC.

Those skilled in the art will recognize that the oligopeptides of the invention are useful in various applications. For example, the oligopeptides may be used in in vitro binding assays to determine their capacity to bind to various sulfated agents. In this way, sulfated agents with a high binding affinity for the oligopeptides, and thus a high potential for binding or binding and inhibiting the enzyme can be identified. Any such sulfated agents would be useful for purifying the enzyme, and those binding the oligopeptide associated with enzyme inhibition will be strong candidates for cholesterol esterase inhibitor development. Thus the oligopeptides of the invention are useful for identifying agents that are useful for purifying or inhibiting pancreatic cholesterol esterase. The oligopeptides of the invention are also useful for therapeutic treatments designed to decrease cholesterol absorption. This is because the oligopeptides are capable of displacing the enzyme from its intestinal cell binding site by competitive binding. Thus the oligopeptides may be incorporated in a pharmaceutically acceptable carrier and administered in an amount effective for reducing cholesterol absorption. Displacement of cholesterol esterase by the oligopeptides may also be useful for enzyme purification purpose by using the oligopeptides to release bound enzyme in affinity chromatography procedures.

Purification of the enzyme takes advantage of the affinity of the enzyme principally through its sulfate binding site, for a sulfated matrix. A solution comprising the pancreatic cholesterol esterase is applied to the sulfated matrix. The solution must be provided at a salt concentration and pH sufficient to allow the pancreatic cholesterol esterase to bind to the sulfated matrix. A variety of low salt concentrations will allow binding. Most preferably, binding is allowed to occur in 25 mM acetate, 50 mM benzamidine at a pH of 5.1. The use of a buffer at this pH and the presence of benzamidine serve to inhibit proteolysis. Prior art procedures have failed to address the problem of proteolysis during purification. This is believed to be the reason that the major form (72 kDa) of the bovine enzyme has never been detected previously, even though it may be related structurally as a derivative of the previously described 67 kDa bovine enzyme.

After binding of the pancreatic cholesterol esterase to the sulfated matrix has occurred, contaminating proteins can be removed by washing the column with a solution at a salt concentration and pH sufficient to allow continued binding of the pancreatic cholesterol esterase to the sulfated matrix. This may be achieved through the use of either a single wash solution or a linear salt gradient. For example, sulfated resins are preferably washed with linear salt gradients, whereas sulfated polysaccharides including cellulose-sulfate and heparin-agarose are most preferably washed with a single wash solution at a higher salt concentration because these matrices bind the enzyme with higher affinity. Pancreatic cholesterol esterase is finally eluted from the sulfated matrix by washing the matrix with a solution at a salt concentration and pH sufficient to inhibit the binding of the enzyme to the sulfated matrix. When a linear salt gradient is employed, fractions are collected and the enzyme will be present in fractions at higher salt concentrations, Alternatively, when sulfated polysaccharides are utilized as the affinity matrix, the enzyme can be collected with a single wash utilizing a solution of a sulfated bile salt, such as taurocholate. Preferred sulfated matrices with conditions for binding and elution are described in Example 5. Combinations of matrices can be used for purification to homogeneity and other preliminary steps may be included. The bovine major (72 kDa) species, for example, was purified by the sequential chromatography steps of S-Sepharose with a linear salt gradient, SP-Sephadex with a linear salt gradient and mono-S with a linear salt gradient. Human pancreatic cholesterol esterase, in contrast, was preliminarily fractionated over hydroxylapatite and AcA-34, followed by purification on heparin-sepharose with a single high salt elution step.

The ability to purify to homogeneity significant quantities of mammalian pancreatic cholesterol esterases in general and human pancreatic cholesterol esterase in particular, allows for the first time on a large scale the production of antibodies to human pancreatic cholesterol esterase, as well as to other mammalian pancreatic cholesterol esterases. The homogeneous enzyme is used to immunize cows which produce antibodies to the enzyme and secrete it into their milk. The antibodies are readily purified from the milk by affinity chromatography using a binding component comprising homogeneous pancreatic cholesterol esterase cross-linked to an inert matrix. In this manner large quantities of purified antibodies highly specific for pancreatic cholesterol esterase are readily prepared. Such antibodies, particularly antibodies to human pancreatic cholesterol esterase, can be used as inhibitors to pancreatic cholesterol esterase and might lead to reduced serum cholesterol levels.

FIG. 1 shows the amino acid sequence deduced from the nucleotide sequence shown in FIG. 2 of bovine pancreatic cholesterol esterase. The amino acid sequence in FIG. 1 further enables the production of antibodies to peptides comprising less than a complete pancreatic cholesterol esterase molecule. Such peptides may be prepared by chemical synthesis or by proteolycic or chemical cleavage of the purified enzyme. The peptides may be used alone to immunize cows or may be coupled to a carrier protein, such as keyhole limpet hemocyanin (KLH). In either case the antibodies would be purified from cow's milk using affinity chromatography with the purified enzyme as the binding component, as described above.

The present invention provides, for the first time, useful quantities of homogeneous pancreatic cholesterol esterase. Thus the homogeneous enzyme composition can be used to screen potential inhibitors of pancreatic cholesterol esterase for their ability to modify enzyme properties, such as release of free cholesterol from fatty acyl cholesterol esters, or binding of immobilized heparin.

The ability to produce useful quantities of this enzyme in pure form further allows for the use of the enzyme in commercial applications. In particular, the purified enzyme will be used to alter the cholesterol/cholesterol ester composition of foodstuffs and biologics through its catalytic function. The bile salt taurocholate is required at concentrations above 1 mM for esterase activity whereas in the absence of taurocholate or in the presence of low concentrations of taurocholate (i.e. less than 250 µM) the enzyme will operate to esterify cholesterol. Thus, both increases and decreases in free cholesterol in biologics or foodstuffs may be moderated by the same enzyme by simply altering the conditions.

The present invention provides also, for the first time, a composition of homogeneous mammalian pancreatic cholesterol esterase, especially the bovine 72 kDa species, in sufficient quantity for amino acid sequence analysis. Those skilled in the art will recognize that the ability to carry out such an analysis greatly enhances the probability of successfully cloning the gene encoding the underlying peptide sequence. Amino acid sequence determination allows the determination of a finite set of nucleotide sequences which can encode a particular peptide, based upon the genetic code. Within such a finite set of nucleotide sequences will be found a smaller set of nucleotide sequences which are more likely to encode the particular peptide, on the basis of the codon usage preference of the organism from which the gene is to be isolated.

Once a tissue source which expresses the protein of interest has been identified, mRNA can be isolated from this source. The mRNA can be used to synthesize cDNA, from which a library can be prepared. A mixture of oligonucleotides corresponding to the subset of nucleotide sequences most likely to encode a peptide from the protein can then be used to screen the library for the presence of a cDNA encoding the protein of interest.

In the case of mammalian pancreatic cholesterol esterase, the pancreas has long been known in the art as the tissue source expressing this enzyme. We have additionally discovered that expression of this enzyme in the pancreas of adult cows greatly exceeds that of calf pancreas. Thus, mRNA was prepared from adult bovine pancreas by standard procedures, and used for the synthesis of cDNA, according to procedures well known in the art. A cDNA library was prepared by conventional methods.

Conventional N-terminal amino acid sequence analysis of the homogeneous composition of bovine pancreatic cholesterol esterase, prepared as described herein, allowed the synthesis of a mixed oligonucleotide probe of the following sequence:

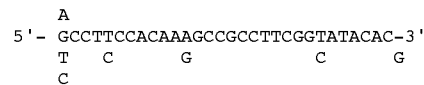

This probe mixture was shown to hybridize very strongly in Northern blots of mRNA isolated from adult bovine pancreas to an mRNA species of 1.9 kb. No detectable hybridization was observed when mRNA isolated from calf pancreas was used. The probe was then used to identify a hybridizing clone from the cDNA library. The clone was isolated and a plasmid containing a full-length cDNA encoding pancreatic cholesterol esterase was excised therefrom. The nucleotide sequence of the cDNA was determined according to procedures well known in the art. The amino acid sequence for the entire bovine protein is shown in FIG. 1, as deduced from the nucleotide sequence shown in FIG. 2. The predicted peptide sequence is 578 amino acids in length and has a molecular weight of 63.5 kDa in the absence of glycosylation. There are two potential N-glycosylation sites. The theoretical isoelectric point of the unglycosylated protein is 5.1.

The cDNA shown in FIG. 2 was then used as a probe to screen a human pancreatic cDNA library. The bovine probe was hybridized to the human pancreatic cDNA library. Positive clones were obtained, including full length clones. Partial DNA sequence analysis confirmed that the clones encoded human pancreatic cholesterol esterase.

Thus, the present invention encompasses a cloned DNA sequence encoding mammalian pancreatic cholesterol esterase. For purposes of defining this aspect of the invention, a cloned DNA sequence will be interpreted to mean a DNA molecule comprising two portions: a (1) specific nucleotide sequence, covalently attached to (2)

another DNA molecule portion which is capable of autonomous replication within a bacterial, yeast, plant, insect or mammalian cell, wherein the autonomously replicating DNA molecule is not a bacterial, yeast, plant, insect or mammalian chromosome, and whereby the cloned DNA sequence and attached autonomously replicating DNA molecule are capable of replicating autonomously as a unit within a bacterial, yeast, plant, insect or mammalian cell. Thus, a cloned DNA sequence may refer to a cloning vector that contains a specific nucleotide sequence encoding a cholesterol esterase. A DNA sequence encoding mammalian pancreatic cholesterol esterase is defined as a DNA sequence which, when transcribed and translated in a cell will give rise to a protein which is capable of releasing oleic acid from cholesteryl oleate, and is also capable of liberating palmitic acid from palmitoyl lysophosphatidyl choline. A representative DNA sequence encoding a mammalian pancreatic cholesterol esterase is the bovine sequence shown in FIG. 2. Those skilled in the art will recognize that the disclosure relating the cloning of this DNA sequence coupled with the DNA sequence shown in FIG. 2 fully enables the cloning of other mammalian pancreatic cholesterol esterases including those from humans, pigs, and rats. DNA sequences encoding any mammalian pancreatic cholesterol esterase as defined above are enabled and contemplated by the present invention.

A recombinant expression vector encoding a mammalian pancreatic cholesterol esterase can readily be prepared by methods well known in the art. Such a vector comprises the DNA sequence encoding a mammalian pancreatic cholesterol esterase, a promoter of other DNA sequence recognized by RNA polymerase as a signal for the initiation of transcription, and an origin of replication which allows the vector to replicate in a bacterial, yeast, plant, insect, or mammalian cell.

Cell culture expression systems have been extensively discussed in the art. Most preferred are mammalian cell culture expression systems, particularly the systems involving CHO(dhfr-) cells. In such a system, a recombinant expression vector encoding and capable of expressing the pancreatic cholesterol esterase can be introduced into CHO (dhfr-) cells together with a plasmid encoding and capable of expressing dhfr. Transfected cells can be selected in selective media, for example hypoxanthine-glycine-thymidine (HGT) media. Subsequent amplification of transfected DNA can be mediated by growing transfected cells in media containing methotrexate. Expression may be assayed by activity assays carried out using culture supernantants or through well established immunological procedures.

The following examples are shown by way of illustration and not by way of limitation.

EXAMPLE 1

Purification of Human Pancreatic Cholesterol Esterase

Human pancreas was received at autopsy. About 30 g of tissue in 10 mM phosphate, pH 6.0, 50 mM benzamidine, 0.5% digitonin were homogenized with a polytron, centrifugally pelleted (48,000×g, 30 min.) and the supernatant collected. The supernatant was centrifugally pelleted (100,000×g, 60 min.) again and the second supernatant was passed through glass wool and dialized overnight against 50 mM benzamidine, 10 mM phosphate, pH 6.8. The dialysate was loaded onto a hydroxylapatite column (2.6×10 cm) equilibrated with 50 mM benzamidine, 10 mM phosphate, pH 6.8. The column was washed with identical buffer, then developed with a linear gradient of 50 mM to 350 mM phosphate, pH 6.8, 50 mM benzamidine. The cholesterol esterase activity eluted at a conductivity of 20–22 mS/cm. These fractions were pooled and loaded onto an AcA34 column (Bio-Rad Laboratories, Inc., 2200 Wright Avenue, Richmond, Calif. 94804) (2.6×90 cm) equilibrated with 500 mM NaCl, 10 mM phosphate, pH 6.0. The fraction emerging at an apparent molecular weight of 350 kDa contained cholesterol esterase activity and was dialyzed against 10 mM phosphate, pH 6.0.

The enzyme was applied to heparin Sepharose (Pharmacia Inc., 800 Centennial Avenue, Piscataway, N.J. 08854) equilibrated with the same buffer. The resin was then washed with five to 10 column volumes of 50 mM NaCl, 50 mM benzamidine, 10 mM Tris, pH 7.2 followed by two column volumes of 20 mM taurocholate, 30 mM NaCl, 50 mM benzamidine, 10 mM Tris, pH 7.2. Purified enzyme is then eluted in 500 mM NaCl, 10 mM Tris, pH 7.2, 50 mM benzamidine.

EXAMPLE 2

Purification of Bovine Pancreatic Cholesterol Esterase

Commercially available bovine pancreatic cholesterol esterase (Sigma Chemical Co., P.O. Box 14509, St. Louis, Mo. 63178; purity <1%) in 10 mM Tris. pH 7.2, was applied to heparin-Sepharose (Pharmacia Inc., 800 Centennial Avenue, Piscataway, N.J. 08854) % 10 cm) equilibrated with the same buffer. The resin was developed further by washing with 0.10 M NaCl, 10 mM Tris, pH 7.2. Little or no activity was found in any of these preliminary steps, even though virtually all of the applied protein was eluted. When the absorbance at 280 nm returned to zero, the resin was washed with 20 mM sodium taurocholate containing sodium chloride to give a conductivity of 13 to 15 mS/cm. the same conductivity as that of the previous washing buffer. All the activity was eluted in several fractions. This single purification step typically provided a 60 to 80% yield with a 50- to 100-fold purification and gives a single band at 67 kDa on SDS-PACE. No additional activity was found when the resin was washed with higher concentrations of salt and the resin could be regenerated by washing with 2.0 M NaCl, 10 mM Tris, pH 7.2. The large purification factor achieved by this single step indicates that heparin is acting as an affinity ligand for cholesterol esterases a property demonstrated further by using different elution conditions. Thus, when the charged resin was washed with heparin (2 mg/ml), greater than 95% of the enzyme was eluted from the resin, while chondroitin sulfate (5 mg/ml), another sulfated mucopolysaccharide, removed less than 2% of bound enzyme.

EXAMPLE 3

Purification of Porcine Pancreatic Cholesterol Esterase

The same procedure described in Example 2 for the human enzyme was used for porcine pancreatic cholesterol esterase. In this case, active enzyme was found at 15 to 17 mS/cm from the hydroxylapatite column, and emerged from the AcA 34 gel filtration column (Bio-Rad Laboratories, 2200 Wright Avenue, Richmond, Calif. 94804) at a molecular weight of 81 kD. This procedure provides homogeneous enzyme with molecular weight 81 kDa in 25% yield.

EXAMPLE 4

Purification of Bovine 72 kDa Major Species Pancreatic Cholesterol Esterase

Supernatant from bovine pancreas homogenate was prepared according to Example 1 as described for the human enzyme. The supernatant was chromatographed over S-Sepharose (Pharmacia Inc., 800 Centennial Avenue, Piscataway, N.J. 08854) in 25 mM acetate pH 5.1, 50 mM benzamidine. The enzyme was eluted from the column using a linear salt gradient from 175 mM NaCl to 500 mM NaCl. The eluate was loaded onto a SP-Sephadex (Pharmacia Inc., 800 Centennial Avenue, Piscataway, N.J. 08854) column in 25 mM acetate, pH 5.1, 50 mM benzanidine, then eluted with a linear gradient of 0 mM to 120 mM NaCl. The eluate contained two bands exhibiting cholesterol esterase activity, one at 72 kDa (90–99%) and one at 67 kDa (1–10%). The 72 kDa form vas completely separated from the 67 kDa form by chromatography over a mono-S column (Pharmacia Inc., 800 Centennial Avenue, Piscataway, N.J. 08854).

EXAMPLE 5

Purification of Cholesterol Esterases Using Sulfated Cellulose Columns

A. Preparation of Sulfated Cellulose Columns

Cellulose was lightly sulfated to maintain its insolubility and this material was used as a potent matrix for isolating and purifying the enzyme. Thus, 2.5 g of cellulose (type 100) was suspended in 50 ml water and 12.5 g of sulfur trioxide pyridine complex were added with stirring. After one hour at room temperature, 100 ml of dimethylformamide were added, and the mixture was stirred for an additional 30 minutes. The cellulose sulfate was collected by centrifugation. After washing six times with water, the resin was packed in a small column (0.9×9 cm).

Resins such as chose described in part A of this example and the other sulfated polysaccharides can be used to purify cholesterol esterases. For example, bovine cholesterol esterase was pumped onto the resin in 25 mM acetate, pH 5.1 at 15 ml/hr All the activity was bound, but in this case, binding was so strong that even 2 M NaCl in 25 mM acetate, pH 5.1 did not remove the enzyme. Elution with 100 mM taurocholate, a sulfated bile salt, removed all the activity in virtually 100% yield. Heparin agarose also functions as an effective affinity matrix for cholesterol esterase in the same manner.

EXAMPLE 6

Assays for Cholesterol Esterase Activity

Cholesterol esterase activity was determined by measuring the release of [$^{14}$C]-oleic acid from vesicles containing cholesteryl 1-[$^{14}$C]-oleate. Vesicles were prepared by drying under nitrogen a solution of 1.00 ml of 1.33 mM egg phosphatidylcholine in hexane and 1.27 ml of 1 mM cholesteryl oleate containing 10 μl of cholesteryl 1-[$^{14}$C]-oleate (2.2×10$^5$ cpm) in chloroform. The precipitate was resuspended in 10 ml of 0.15 M Tris, pH 7.5, vortexed vigorously for several seconds and then sonicated on ice for 20 minutes under nitrogen. Following sonication, the preparation was centrifuged at 48,000×g for 60 minutes, and the vesicle preparation was carefully decanted and stored at 4° C. In a typical assay, 75 μl of cholesteryl [$^{14}$C]-oleate vesicles, 25 μl of 100 mM taurocholate, 175 μl of 0.15 M Tris, pH 7.5 were mixed in a test tube and hydrolysis was initiated by adding 25 μl of enzyme to the reaction mixture at 37° C. After a known time, usually five minutes, the reaction was quenched by addition of 600 μl of 0.3 N NaOH and 3 ml of benzene:methanol:chloroform (1:1.2:0.5). After mixing, the samples were centrifuged and 1 ml of the clear organic phase was removed and counted for radioactivity. Since only part of the sample was removed for counting, an efficiency sample was prepared by adding 100 μl of [$^{14}$C]-oleic acid vesicles of known specific radioactivity to 200 μl of 0.15 M Tris, pH 7.5. The same manipulations were performed on this sample as those described above for assay. The efficiency of transfer was then determined by dividing the number of counts in the 1 ml organic phase by the dpm in 100 μl of starting [$^{14}$C]-oleic acid vesicles. Activity is expressed as nanomoles of oleic acid released/ml/hour and was less than 0.1 nmol/ml/hr in the absence of added enzyme. To assess the potential inhibition of chemical compounds, these agents are added to the incubation mixture before addition of cholesterol esterase and the ratio of [$^{14}$C]-oleate release determined as above and compared to the ratio observed in the absence of the rest compound.

EXAMPLE 7

Preparation of Rabbit IgG Fraction Against 67 kDa Bovine Pancreatic Cholesterol Esterase Five hundred micrograms of homogeneous 67 kDa protein were emulsified in Freund's complete adjuvant (CFA) and injected subcutaneously into a New Zealand White rabbit. Twenty-one days later the rabbit was boosted with intraperitoneal injections of 250 μg protein dissolved in 1 ml of 10 mM sodium phosphate 150 mM NaCl, pH 7.1. The rabbits were bled 10 days later and the presence of anti-cholesterol IgG was determined on Ouchterlony plates. Rabbit IgG was purified by passing 20 ml of rabbit serum over a protein A Sepharose (Pharmacia, Inc., 800 Centennial Avenue, Piscataway, N.J. 08854) column equilibrated with 20 mM Tris 20 mM NaCl, pH 8.0. The resin was washed with equilibration buffer followed by 20 mM Tris 0.5% deoxycholate, 500 mM NaCl, pH 8.0 and then equilibration buffer. Finally, the IgG was eluted with 100 mM glycine pH 2.8. Similarly, 2 mg of homnogeneous human cholesterol esterase emulsified in CFA are injected into four subcutaneous sites in a cow, and booster injections of 1 mg protein at three and six weeks are made. Secretory antibodies are elicited in the cow's milk that are directed at human cholesterol esterase and can be separated from other milk proteins by ammonium sulfate precipitation and ion-exchange chromatography.

EXAMPLE 8

Construction and Screening of Bovine Pancreas cDNA Library

A. Construction of Bovine Pancreas cDNA Library

Total RNA was extracted from bovine pancreas with 5.5 M guanidine thiocyanate, as described by Han et al., 1987, Biochemistry 26: 1617–1625; poly A$^+$ RNA was purified from total RNA by chromatography on oligo dT-cellulose (Pharmacia Inc., 800 Centennial Avenue, Piscataway, N.J. 08854). A cDNA library was constructed using 5 μg of twice-selected poly A$^+$ RNA using a Pharmacia cDNA synthesis kit according to the method of Gubler and Hoffman, 1983, Gene 25: 263–269. The EcoRI-ended double-stranded cDNA was ligated into EcoRI-digested and dephosphorylated λ-ZAP vector arms (Stratagene 11099 North Torrey Pines Road, La Jolla, Calif. 92037), and packaged using a Stratagene kit. About 300,000 to 500,000 independent, recombinant clones were obtained.

B. Preparation of Probe for Screening the cDNA Library

Total RNA and poly A$^+$ RNA were isolated from pancreas of adult cow or calf as described in part A of this example.

RNA was denatured with formaldehyde and formamide and electrophoresed on a 11 agarose-formaldehyde gel containing 2.2 M formaldehyde. RNA was transferred by capillary action to a nylon membrane (Schleicher and Schuell, Inc., 10 Optical Avenue, Keene, N.H. 03431) in 20×SSPE. A 30-mer probe mixture was synthesized based upon N-terminal amino acid sequence determined from purified bovine pancreatic cholesterol esterase. The probe mixture:

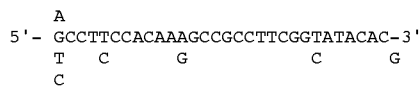

was labelled using α-[$^{32}$P]-ATP and polynucleotide kinase. The probe mixture hybridized strongly to a single 1.9 kb band in lanes containing total RNA or poly A$^+$ RNA from adult bovine pancreas, but did not hybridize to lanes containing total RNA or poly A$^+$ RNA from calf pancreas.

C. Screening Bovine Pancreas cDNA Library

The radiolabelled probe described in part B of this example was used to probe the cDNA library constructed as described in part A of this example. The library was screened by plaque hybridization in the presence of 0.25% nonfat dry milk in 6×SSPE. Prehybridization and hybridization were conducted at 60° C. A bluescript plasmid was excised from the hybridizing λ-Zap clones by co-infecting XLI-Blue cells with positive λ-Zap phage and R-408 helper phage. Excision from the plasmid of a cDNA clone encoding the entire cholesterol esterase protein was performed, with identification in the cDNA sequence of both the N-terminal protein sequence and the sequence of the 30-mer probe given in part B of this example. Bluescript plasmids were harvested by the alkaline lysis method of Birnboin, 1983, Meth. Enzymol. 100: 243–255.

EXAMPLE 9

DNA Sequence Analysis of cDNA for Cholesterol Esterase

Each sequencing reaction used approximately 3 μg of double-stranded pBluescript plasmid with positive inserts and 50 ng of sequencing primer. Double-stranded plasmid was denatured for 5 minutes at room temperature with 0.2 M NaOH, 0.2 mM ethylene diamine tatraacetate (EDTA) (final concentrations); DNA was precipitated with 0.18 M ammonium acetate, pH 5.4 (final concentration) and 2.5 volumes of ethanol. The mixture was chilled on dry ice for 15 minutes and the DNA pellet was spun down for 10 minutes in a microfuge. The pellets were washed with 70% ethanol and vacuum dried. The inserts were sequenced by the dideoxy chain termination method of Sanger et. al., 1977, Proc. Natl. Acad. Sci. USA 74: 5463–5467 using Sequenase™ 2.0 (U.S. Biochemical Corporation, P. O. Box 22400, Cleveland, Ohio 44122) or AMV reverse transcriptase sequencing kit (Stratagene, 11099 North Torrey Pines Road, LA Jolla, Calif. 92037). Internal sequences for both strands were obtained by sequential nested primers, 18 to 20 nucleotides in length. The DNA sequence thus obtained is shown in FIG. 2.

EXAMPLE 10

Construction of Expression Vectors

The eukaryotic-prokaryotic shuttle vector pSV2neo has been described by Southern and Berg, (1982) J. Mol. App. Genet. 2: 327–341. A vector capable of expressing bovine pancreatic cholesterol esterase in mammalian cells is prepared by inserting the full-length cDNA (FIG. 2) isolated as described in Example 8, into pSV2neo in such a way as to replace the neo gene, and thus be flanked by the SV-40 early promoter upstream and the SV-40 polyadenylation signal downstream. The insert in the cDNA clone is first site-directed mutagenized to remove a single EcoRI restriction site within the cDNA and then the insert is removed by digesting the cDNA clone with EcoRI. The 1.9 kb insert is isolated by electroelution. The EcoRI ends are converted to blunt ends by incubation of the DNA fragment in the presence of Klenow polymerase and 10 μm dNTPS for 5 minutes. The neo gene is removed from pSV2neo by digestion with HindIII and SmaI and the 4.4 kb vector fragment is isolated by electroelution. The HindIII end is converted to a blunt end using Klenow polymerase. The isolated and blunt-ended fragments are then digested together by the use of T4 DNA ligase and T4RNA ligase (10:1 unit ratio) in the presence of 100 μm ATP and 50 mM MgCl$_2$ at room temperature for about three hours. A portion of the ligation mixture is used to transform competent HB101 E. coli bacteria, which are selected for ampicillin resistance. The orientation of the insert is determined by DNA sequencing, as described in Example 9.

EXAMPLE 11

Expression of Bovine Pancreatic Cholesterol Esterase in CHO Cells

The expression vector described in Example 10 is co-introduced into DHFR deficient CHO cells along with a plasmid expressing the DHFR gene, by the method of Graham and Van der Eb, 1973, J. Virology 52: 456–467. The plasmid expressing DHFR is prepared as described in Example 10, except that the DHFR gene from the plasmid pE342.HBV.E400.D22 is used in place of the bovine pancreatic cholesterol esterase gene. The plasmid pE342.HBV.E400.D22 is described in U.S. Pat. No. 4,850,330. Transfected cells are selected in HGT medium. Resistant colonies are tested for expression of pancreatic cholesterol esterase by collecting their media supernatants and utilizing them in the assay described in Example 6. Clones found to be expressing cholesterol esterase are seeded at 200,000 cells per 100 nM plate in 50 mM methotrexate (MTX) to select for DNA amplification. Cells surviving the initial MTX selection are tested again for cholesterol esterase activity. Those cells showing an increase in cholesterol esterase activity, relative to pre-amplification activity levels, are then further selected for amplification in 500 nM MTX. Resistant cells shoving additional increases in cholesterol esterase activity are finally selected for optimum amplification in 10,000 nM MTX. Those subclones resistant to 10,000 nM MTX which produce the highest levels of cholesterol esterase activity are used as producer cell lines to provide cholesterol esterase which, after purification as described in Example 4, can be used to screen for enzyme inhibitors, produce anti-enzyme antibodies or alter the cholesterol/cholesterol ester composition of foodstuffs.

EXAMPLE 12

Synthesis of Cholesterol Esters by Cholesterol Esterase

Bovine pancreatic cholesterol esterase was incubated at pH 6.0 with 900 μm $^{14}$C-oleate and 700 μm cholesterol or with cholesteryl-[$^{14}$C]-oleate, at varying concentrations of the bile salt taurocholate. Ester synthesis in the former case was assayed by determining the rate of formation of cholesteryl-[$^{14}$C]-oleate and in the latter case as described in Example 6. The synthesis and hydrolytic rates and the ratios between them at various concentrations of taurocholate are shown below in Table I. Rates are expressed as μmoles of product formed per mg of enzyme per hour.

TABLE I

| | Taurocholate, mM | | | |
|---|---|---|---|---|
| | 0 | 0.1 | 1.0 | 10.0 |
| Synthetic | 0.83 | 14.2 | 32.5 | 78.3 |
| Hydrolytic | 0 | 0 | 12.0 | 73.5 |
| Ratio+ | — | — | 2.7 | 1.1 |

These results indicate that the enzyme can be made to act primarily as a synthetic enzyme at appropriate concentrations of taurocholate below 1 mM. Thus, the enzyme can be used to alter the cholesterol/cholesterol ester composition of a given solution by simply adding enzyme and adjusting the level of taurocholate from 0 to 1 mM. Above 1 mM taurocholate, the enzyme is useful for the general hydrolysis of cholesterol esters. Thus, free cholesterol in foodstuffs such as liquid dairy products can be converted into esterified cholesterol, which may be more poorly absorbed than free cholesterol or whose absorption may be inhibited through the oral ingestion of sulfated polysaccharides (see, for example, U.S. Ser. Nos. 340,868, 425,109 and co-pending U.S. application entitled, "The Use of Sulfated Polysaccharides To Decrease Cholesterol and Fatty Acid Absorption", filed Oct. 31, 1989, all of which are hereby incorporated by reference).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for producing antibodies to a mammalian pancreatic cholesterol esterase, the method comprising the following steps:

(a) immunizing cows with a homogeneous composition of a mammalian pancreatic cholesterol esterase, purified by the method comprising the steps of;
        (1) loading a solution consisting of cholesterol esterase and contaminating proteins on a sulfated matrix, wherein the concentration of the salt and the pH of the solution comprising the cholesterol esterase is sufficient to allow the cholesterol esterase to bind the sulfated matrix and benzamidine is included in the solution to inhibit proteolysis;
        (2) removing non-binding contaminating proteins by washing the matrix with a solution comprising a concentration of salt and pH sufficient to allow continued binding of the cholesterol esterase to the matrix; and
        (3) eluting the cholesterol esterase from the matrix by washing the matrix with a solution comprising a concentration of salt and pH sufficient to inhibit binding of the cholesterol esterase to the matrix;
    (b) collecting the milk from the cows; and
    (c) purifying the antibodies from the milk by affinity chromatography using the mammalian pancreatic cholesterol esterase as the binding component for affinity chromatography.

2. The method according to claim 1, wherein the mammalian pancreatic cholesterol esterase is human pancreatic cholesterol esterase.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 597 amino acids
        (B) TYPE: amino acid
        (D) TOPOLOGY: linear (ii) MOLECULE TYPE: protein (ix) FEATURE:
        (A) NAME/KEY: misc_feature
        (B) LOCATION: 1..597
        (D) OTHER INFORMATION: /note= "Bovine pancreatic cholesterol esterase"

(xi) SEQUENCE DESCRIPTION: SEQ ID NO:1:

```
Leu Gly Ala Ser Arg Leu Gly Pro Ser Pro Gly Cys Leu Ala Val Ala
 1               5                  10                  15

Ser Ala Ala Lys Leu Gly Ser Val Tyr Thr Glu Gly Gly Phe Val Glu
            20                  25                  30

Gly Val Asn Lys Lys Leu Ser Leu Phe Gly Asp Ser Val Asp Ile Phe
        35                  40                  45

Lys Gly Ile Pro Phe Ala Ala Ala Pro Lys Ala Leu Glu Lys Pro Glu
    50                  55                  60

Arg His Pro Gly Trp Gln Gly Thr Leu Lys Ala Lys Ser Phe Lys Lys
65                  70                  75                  80

Arg Cys Leu Gln Ala Thr Leu Thr Gln Asp Ser Thr Tyr Gly Asn Glu
                85                  90                  95

Asp Cys Leu Tyr Leu Asn Ile Trp Val Pro Gln Gly Arg Lys Glu Val
            100                 105                 110

Ser His Asp Leu Pro Val Met Ile Trp Ile Tyr Gly Gly Ala Phe Leu
        115                 120                 125

Met Gly Ala Ser Gln Gly Ala Asn Phe Leu Ser Asn Tyr Leu Tyr Asp
    130                 135                 140

Gly Glu Glu Ile Ala Thr Arg Gly Asn Val Ile Val Val Thr Phe Asn
145                 150                 155                 160

Tyr Arg Val Gly Pro Leu Gly Phe Leu Ser Thr Gly Asp Ser Asn Leu
```

-continued

```
                165                 170                 175
Pro Gly Asn Tyr Gly Leu Trp Asp Gln His Met Ala Ile Ala Trp Val
                180                 185                 190
Lys Arg Asn Ile Glu Ala Phe Gly Gly Asp Pro Asp Asn Ile Thr Leu
                195                 200                 205
Phe Gly Glu Ser Ala Gly Gly Ala Ser Val Ser Leu Gln Thr Leu Ser
                210                 215                 220
Pro Tyr Asn Lys Gly Leu Ile Lys Arg Ala Ile Ser Gln Ser Gly Val
225                 230                 235                 240
Gly Leu Cys Pro Trp Ala Ile Gln Gln Asp Pro Leu Phe Trp Ala Lys
                245                 250                 255
Arg Ile Ala Glu Lys Val Gly Cys Pro Val Asp Asp Thr Ser Lys Met
                260                 265                 270
Ala Gly Cys Leu Lys Ile Thr Asp Pro Arg Ala Leu Thr Leu Ala Tyr
                275                 280                 285
Lys Leu Pro Leu Gly Ser Thr Glu Tyr Pro Lys Leu His Tyr Leu Ser
                290                 295                 300
Phe Val Pro Val Ile Asp Gly Asp Phe Ile Pro Asp Asp Pro Val Asn
305                 310                 315                 320
Leu Tyr Ala Asn Ala Ala Asp Val Asp Tyr Ile Ala Gly Thr Asn Asp
                325                 330                 335
Met Asp Gly His Leu Phe Val Gly Met Asp Val Pro Ala Ile Asn Ser
                340                 345                 350
Asn Lys Gln Asp Val Thr Glu Glu Asp Phe Tyr Lys Leu Val Ser Gly
                355                 360                 365
Leu Thr Val Thr Lys Gly Leu Arg Gly Ala Asn Ala Thr Tyr Glu Val
                370                 375                 380
Tyr Thr Glu Pro Trp Ala Gln Asp Ser Ser Gln Glu Thr Arg Lys Lys
385                 390                 395                 400
Thr Met Val Asp Leu Glu Thr Asp Ile Leu Phe Leu Ile Pro Thr Lys
                405                 410                 415
Ile Ala Val Ala Gln His Lys Ser His Ala Lys Ser Ala Asn Thr Tyr
                420                 425                 430
Thr Tyr Leu Phe Ser Gln Pro Ser Arg Met Pro Ile Tyr Pro Lys Trp
                435                 440                 445
Met Gly Ala Asp His Ala Asp Asp Leu Gln Tyr Val Phe Gly Lys Pro
450                 455                 460
Phe Ala Thr Pro Leu Gly Tyr Arg Ala Gln Asp Arg Thr Val Ser Lys
465                 470                 475                 480
Ala Met Ile Ala Tyr Trp Thr Asn Phe Ala Arg Thr Gly Asp Pro Asn
                485                 490                 495
Thr Gly His Ser Thr Val Pro Ala Asn Trp Asp Pro Tyr Thr Leu Glu
                500                 505                 510
Asp Asp Asn Tyr Leu Glu Ile Asn Lys Gln Met Asp Ser Asn Ser Met
                515                 520                 525
Lys Leu His Leu Arg Thr Asn Tyr Leu Gln Phe Trp Thr Gln Thr Tyr
                530                 535                 540
Gln Ala Leu Pro Thr Val Thr Ser Ala Gly Ala Ser Leu Leu Pro Pro
545                 550                 555                 560
Glu Asp Asn Ser Gln Ala Ser Pro Val Pro Pro Ala Asp Asn Ser Gly
                565                 570                 575
Ala Pro Thr Glu Pro Ser Ala Gly Asp Ser Glu Val Ala Gln Met Pro
                580                 585                 590
```

```
Val Val Ile Gly Phe
        595
```

(2) INFORMATION FOR SEQ ID NO:2:

(i) SEQUENCE CHARACTERISTICS:
        (A) LENGTH: 1908 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 100..129
        (D) OTHER INFORMATION: /note= "complementary sequence to
            oligonucleotide probe"

(ix) FEATURE:
        (A) NAME/KEY: CDS
        (B) LOCATION: 1..1824

(ix) FEATURE:
        (A) NAME/KEY: misc_feature
        (B) LOCATION: 1..1908
        (D) OTHER INFORMATION: /note= "Bovine pancreatic
            cholesterol esterase cDNA"

(ix) FEATURE:
        (A) NAME/KEY: sig_peptide
        (B) LOCATION: 1..30

(ix) FEATURE:
        (A) NAME/KEY: mat_peptide
        (B) LOCATION: 31..1821

(xi) SEQUENCE DESCRIPTION: SEQ ID NO:2:

```
GCC TAG AGG CAG ACA CTG ACT ATG GGG CGG CTG GGA GCT AGC CGT CTT      48
Ala  *  Arg Gln Thr Leu Thr Met Gly Arg Leu Gly Ala Ser Arg Leu
-10          -5                   1                   5

GGG CCG TCG CCT GGC TGC TTG GCA GTA GCG AGT GCA GCG AAG TTG GGC      96
Gly Pro Ser Pro Gly Cys Leu Ala Val Ala Ser Ala Ala Lys Leu Gly
             10                  15                  20

TCC GTA TAC ACC GAA GGC GGC TTC GTG GAG GGC GTC AAC AAG AAG CTG     144
Ser Val Tyr Thr Glu Gly Gly Phe Val Glu Gly Val Asn Lys Lys Leu
         25                  30                  35

AGC CTC TTT GGC GAC TCT GTT GAC ATC TTC AAG GGC ATC CCC TTC GCT     192
Ser Leu Phe Gly Asp Ser Val Asp Ile Phe Lys Gly Ile Pro Phe Ala
     40                  45                  50

GCC GCC CCC AAG GCC CTG GAG AAG CCC GAG CGA CAC CCC GGC TGG CAA     240
Ala Ala Pro Lys Ala Leu Glu Lys Pro Glu Arg His Pro Gly Trp Gln
 55                  60                  65                  70

GGG ACC CTG AAG GCC AAG AGC TTT AAG AAA CGG TGC CTG CAG GCC ACG     288
Gly Thr Leu Lys Ala Lys Ser Phe Lys Lys Arg Cys Leu Gln Ala Thr
                 75                  80                  85

CTC ACG CAG GAC AGC ACC TAC GGA AAT GAA GAC TGC CTC TAC CTC AAC     336
Leu Thr Gln Asp Ser Thr Tyr Gly Asn Glu Asp Cys Leu Tyr Leu Asn
             90                  95                 100

ATC TGG GTC CCC CAG GGC AGG AAG GAA GTC TCC CAC GAC CTG CCC GTC     384
Ile Trp Val Pro Gln Gly Arg Lys Glu Val Ser His Asp Leu Pro Val
        105                 110                 115

ATG ATC TGG ATC TAT GGA GGC GCC TTC CTC ATG GGG GCC AGC CAA GGG     432
Met Ile Trp Ile Tyr Gly Gly Ala Phe Leu Met Gly Ala Ser Gln Gly
    120                 125                 130

GCC AAC TTT CTC AGC AAC TAC CTC TAC GAC GGG GAG GAG ATT GCC ACA     480
Ala Asn Phe Leu Ser Asn Tyr Leu Tyr Asp Gly Glu Glu Ile Ala Thr
135                 140                 145                 150
```

-continued

| | | | | | | | | | | | | | |
|---|---|---|---|---|---|---|---|---|---|---|---|---|---|
| CGG | GGC | AAC | GTC | ATC | GTG | GTC | ACG | TTC | AAC | TAC | CGC | GTT | GGG | CCC | CTG | 528
| Arg | Gly | Asn | Val | Ile | Val | Val | Thr | Phe | Asn | Tyr | Arg | Val | Gly | Pro | Leu |
| | | | 155 | | | | | 160 | | | | | 165 | | |

```
CGG GGC AAC GTC ATC GTG GTC ACG TTC AAC TAC CGC GTT GGG CCC CTG    528
Arg Gly Asn Val Ile Val Val Thr Phe Asn Tyr Arg Val Gly Pro Leu
            155             160                 165

GGC TTT CTC AGC ACC GGG GAC TCC AAC CTG CCA GGT AAC TAT GGC CTT    576
Gly Phe Leu Ser Thr Gly Asp Ser Asn Leu Pro Gly Asn Tyr Gly Leu
            170             175                 180

TGG GAT CAG CAC ATG GCC ATT GCT TGG GTG AAG AGG AAC ATT GAG GCC    624
Trp Asp Gln His Met Ala Ile Ala Trp Val Lys Arg Asn Ile Glu Ala
            185             190                 195

TTC GGA GGA GAC CCC GAC AAC ATC ACC CTC TTT GGG GAG TCG GCC GGA    672
Phe Gly Gly Asp Pro Asp Asn Ile Thr Leu Phe Gly Glu Ser Ala Gly
200             205                 210

GGC GCC AGC GTC TCT CTG CAG ACC CTC TCT CCC TAC AAC AAG GGC CTC    720
Gly Ala Ser Val Ser Leu Gln Thr Leu Ser Pro Tyr Asn Lys Gly Leu
215             220                 225                 230

ATC AAG CGA GCC ATC AGC CAG AGT GGA GTG GGT TTG TGC CCT TGG GCC    768
Ile Lys Arg Ala Ile Ser Gln Ser Gly Val Gly Leu Cys Pro Trp Ala
                235                 240                 245

ATC CAG CAG GAC CCC CTC TTC TGG GCT AAA AGG ATT GCA GAG AAG GTG    816
Ile Gln Gln Asp Pro Leu Phe Trp Ala Lys Arg Ile Ala Glu Lys Val
            250                 255             260

GGC TGC CCC GTG GAC GAC ACC AGC AAG ATG GCT GGG TGT CTG AAG ATC    864
Gly Cys Pro Val Asp Asp Thr Ser Lys Met Ala Gly Cys Leu Lys Ile
            265                 270                 275

ACT GAC CCC CGT GCC CTG ACG CTG GCC TAT AAG CTG CCC CTG GGA AGC    912
Thr Asp Pro Arg Ala Leu Thr Leu Ala Tyr Lys Leu Pro Leu Gly Ser
280                 285                 290

ACG GAA TAC CCC AAG CTG CAC TAT CTG TCC TTC GTC CCC GTC ATC GAT    960
Thr Glu Tyr Pro Lys Leu His Tyr Leu Ser Phe Val Pro Val Ile Asp
295             300                 305                 310

GGA GAC TTC ATC CCT GAT GAC CCC GTC AAC CTG TAC GCC AAC GCC GCG    1008
Gly Asp Phe Ile Pro Asp Asp Pro Val Asn Leu Tyr Ala Asn Ala Ala
                315                 320                 325

GAC GTC GAC TAC ATA GCG GGC ACC AAT GAC ATG GAC GGC CAC CTC TTT    1056
Asp Val Asp Tyr Ile Ala Gly Thr Asn Asp Met Asp Gly His Leu Phe
            330                 335                 340

GTC GGG ATG GAC GTG CCA GCC ATC AAC AGC AAC AAA CAG GAC GTC ACG    1104
Val Gly Met Asp Val Pro Ala Ile Asn Ser Asn Lys Gln Asp Val Thr
            345                 350                 355

GAG GAG GAC TTC TAT AAG CTG GTC AGC GGG CTC ACC GTC ACC AAG GGG    1152
Glu Glu Asp Phe Tyr Lys Leu Val Ser Gly Leu Thr Val Thr Lys Gly
360                 365                 370

CTC AGA GGT GCC AAT GCC ACG TAC GAG GTG TAC ACC GAG CCC TGG GCC    1200
Leu Arg Gly Ala Asn Ala Thr Tyr Glu Val Tyr Thr Glu Pro Trp Ala
375             380                 385                 390

CAG GAC TCA TCC CAG GAG ACC AGG AAG AAG ACC ATG GTG GAC CTG GAG    1248
Gln Asp Ser Ser Gln Glu Thr Arg Lys Lys Thr Met Val Asp Leu Glu
                395                 400                 405

ACT GAC ATC CTC TTC CTG ATC CCC ACA AAG ATT GCC GTG GCC CAG CAC    1296
Thr Asp Ile Leu Phe Leu Ile Pro Thr Lys Ile Ala Val Ala Gln His
            410                 415                 420

AAG AGC CAC GCC AAG AGC GCC AAC ACC TAC ACC TAC CTG TTC TCC CAA    1344
Lys Ser His Ala Lys Ser Ala Asn Thr Tyr Thr Tyr Leu Phe Ser Gln
            425                 430                 435

CCG TCT CGG ATG CCC ATC TAC CCC AAG TGG ATG GGG GCT GAC CAC GCC    1392
Pro Ser Arg Met Pro Ile Tyr Pro Lys Trp Met Gly Ala Asp His Ala
            440                 445                 450

GAT GAC CTC CAG TAT GTC TTC GGG AAG CCC TTC GCC ACC CCC CTG GGC    1440
Asp Asp Leu Gln Tyr Val Phe Gly Lys Pro Phe Ala Thr Pro Leu Gly
455                 460                 465                 470
```

| | | | | | | | | | | | | | | |
|---|---|---|---|---|---|---|---|---|---|---|---|---|---|---|
| TAC | CGG | GCC | CAA | GAC | AGG | ACT | GTG | TCC | AAG | GCC | ATG | ATT | GCC | TAC | TGG | 1488 |
| Tyr | Arg | Ala | Gln | Asp | Arg | Thr | Val | Ser | Lys | Ala | Met | Ile | Ala | Tyr | Trp | |
| | | | 475 | | | | | 480 | | | | | | 485 | | |

```
TAC CGG GCC CAA GAC AGG ACT GTG TCC AAG GCC ATG ATT GCC TAC TGG      1488
Tyr Arg Ala Gln Asp Arg Thr Val Ser Lys Ala Met Ile Ala Tyr Trp
            475                 480                 485

ACC AAC TTT GCC AGA ACT GGG GAC CCT AAC ACG GGC CAC TCG ACA GTG      1536
Thr Asn Phe Ala Arg Thr Gly Asp Pro Asn Thr Gly His Ser Thr Val
        490                 495                 500

CCC GCA AAC TGG GAT CCC TAC ACC CTG GAA GAT GAC AAC TAC CTG GAA      1584
Pro Ala Asn Trp Asp Pro Tyr Thr Leu Glu Asp Asp Asn Tyr Leu Glu
        505                 510                 515

ATC AAC AAG CAG ATG GAC AGC AAC TCT ATG AAG CTG CAT CTG AGG ACC      1632
Ile Asn Lys Gln Met Asp Ser Asn Ser Met Lys Leu His Leu Arg Thr
        520                 525                 530

AAC TAC CTG CAG TTC TGG ACC CAG ACC TAC CAG GCC CTG CCC ACG GTG      1680
Asn Tyr Leu Gln Phe Trp Thr Gln Thr Tyr Gln Ala Leu Pro Thr Val
535                 540                 545                 550

ACC AGC GCG GGG GCC AGC CTG CTG CCC CCC GAG GAC AAC TCT CAG GCC      1728
Thr Ser Ala Gly Ala Ser Leu Leu Pro Pro Glu Asp Asn Ser Gln Ala
        555                 560                 565

AGC CCC GTG CCC CCA GCG GAC AAC TCC GGG GCT CCC ACC GAA CCC TCT      1776
Ser Pro Val Pro Pro Ala Asp Asn Ser Gly Ala Pro Thr Glu Pro Ser
        570                 575                 580

GCG GGT GAC TCT GAG GTG GCT CAG ATG CCT GTC GTC ATT GGT TTC          1821
Ala Gly Asp Ser Glu Val Ala Gln Met Pro Val Val Ile Gly Phe
        585                 590                 595

TAATGTCCTT GGCCTCCAGG GGCCACAGGA GACCCCAGGG CCCACTTCCC               1871

TTCCCAAGTG CCTCCTGAAT AAAGCCTCAA CCATCTC                             1908

(2) INFORMATION FOR SEQ ID NO:3:

(i) SEQUENCE CHARACTERISTICS:
        (A) LENGTH: 605 amino acids
        (B) TYPE: amino acid
        (D) TOPOLOGY: linear (ii) MOLECULE TYPE: protein (xi) SEQUENCE DESCRIPTION: SEQ ID NO:3:

Arg Gln Thr Leu Thr Met Gly Arg Leu Gly Ala Ser Arg Leu Gly Pro
            -5                  1                   5

Ser Pro Gly Cys Leu Ala Val Ala Ser Ala Ala Lys Leu Gly Ser Val
        10                  15                  20

Tyr Thr Glu Gly Gly Phe Val Glu Gly Val Asn Lys Lys Leu Ser Leu
25                  30                  35                  40

Phe Gly Asp Ser Val Asp Ile Phe Lys Gly Ile Pro Phe Ala Ala Ala
            45                  50                  55

Pro Lys Ala Leu Glu Lys Pro Glu Arg His Pro Gly Trp Gln Gly Thr
        60                  65                  70

Leu Lys Ala Lys Ser Phe Lys Lys Arg Cys Leu Gln Ala Thr Leu Thr
        75                  80                  85

Gln Asp Ser Thr Tyr Gly Asn Glu Asp Cys Leu Tyr Leu Asn Ile Trp
        90                  95                  100

Val Pro Gln Gly Arg Lys Glu Val Ser His Asp Leu Pro Val Met Ile
105                 110                 115                 120

Trp Ile Tyr Gly Gly Ala Phe Leu Met Gly Ser Gly Gln Gly Ala Asn
                125                 130                 135

Phe Leu Lys Asn Tyr Leu Tyr Asp Gly Glu Glu Ile Ala Thr Arg Gly
            140                 145                 150

Asn Val Ile Val Val Thr Phe Asn Tyr Arg Val Gly Pro Leu Gly Phe
        155                 160                 165
```

-continued

```
Leu Ser Thr Gly Asp Ser Asn Leu Pro Gly Asn Tyr Gly Leu Trp Asp
    170                 175                 180

Gln His Met Ala Ile Ala Trp Val Lys Arg Asn Ile Glu Ala Phe Gly
185                 190                 195

Gly Asp Pro Asp Asn Ile Thr Leu Phe Gly Glu Ser Ala Gly Gly Ala
200                 205                 210                 215

Ser Val Ser Leu Gln Thr Leu Ser Pro Tyr Asn Lys Gly Leu Ile Lys
                220                 225                 230

Arg Ala Ile Ser Gln Ser Gly Val Gly Leu Cys Pro Trp Ala Ile Gln
            235                 240                 245

Gln Asp Pro Leu Phe Trp Ala Lys Arg Ile Ala Glu Lys Val Gly Cys
        250                 255                 260

Pro Val Asp Asp Thr Ser Lys Met Ala Gly Cys Leu Lys Ile Thr Asp
265                 270                 275                 280

Pro Arg Ala Leu Thr Leu Ala Tyr Lys Leu Pro Leu Gly Ser Thr Glu
                285                 290                 295

Tyr Pro Lys Leu His Tyr Leu Ser Phe Val Pro Val Ile Asp Gly Asp
                300                 305                 310

Phe Ile Pro Asp Asp Pro Val Asn Leu Tyr Ala Asn Ala Ala Asp Val
            315                 320                 325

Asp Tyr Ile Ala Gly Thr Asn Asp Met Asp Gly His Leu Phe Val Gly
        330                 335                 340

Met Asp Val Pro Ala Ile Asn Ser Asn Lys Gln Asp Val Thr Glu Glu
345                 350                 355                 360

Asp Phe Tyr Lys Leu Val Ser Gly Leu Thr Val Thr Lys Gly Leu Arg
                365                 370                 375

Gly Ala Asn Ala Thr Tyr Glu Val Tyr Thr Glu Pro Trp Ala Gln Asp
            380                 385                 390

Ser Ser Gln Glu Thr Arg Lys Lys Thr Met Val Asp Leu Glu Thr Asp
        395                 400                 405

Ile Leu Phe Leu Ile Pro Thr Lys Ile Ala Val Ala Gln His Lys Ser
    410                 415                 420

His Ala Lys Ser Ala Asn Thr Tyr Thr Tyr Cys Phe Ser Gln Pro Ser
425                 430                 435                 440

Arg Met Pro Ile Tyr Pro Lys Trp Met Gly Ala Asp His Ala Asp Asp
                445                 450                 455

Leu Gln Tyr Val Phe Gly Lys Pro Phe Ala Thr Pro Leu Gly Tyr Arg
                460                 465                 470

Ala Gln Asp Arg Thr Val Ser Lys Ala Met Ile Ala Tyr Trp Thr Asn
            475                 480                 485

Phe Ala Arg Thr Gly Asp Pro Asn Thr Gly His Ser Thr Val Pro Ala
        490                 495                 500

Asn Trp Asp Pro Tyr Thr Leu Glu Asp Asp Asn Tyr Leu Glu Ile Asn
505                 510                 515                 520

Lys Gln Met Asp Ser Asn Ser Met Lys Leu His Leu Arg Thr Asn Tyr
                525                 530                 535

Leu Gln Phe Trp Thr Gln Thr Tyr Gln Ala Leu Pro Thr Val Thr Ser
                540                 545                 550

Ala Gly Ala Ser Leu Leu Pro Pro Glu Asp Asn Ser Gln Ala Ser Pro
            555                 560                 565

Val Pro Pro Ala Asp Asn Ser Gly Ala Pro Thr Glu Pro Ser Ala Gly
        570                 575                 580

Asp Ser Glu Val Ala Gln Met Pro Val Val Ile Gly Phe
```

585              590              595

(2) INFORMATION FOR SEQ ID NO:4:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Met Asp Gly His Leu Phe Ala Thr Val Asp Val Pro Ala Ile Asp
1               5                   10                  15

Lys Ala Lys Gln Asp Val
            20

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Lys Lys Arg Cys Leu Gln
1               5

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Pro Ala Ile Asn Lys Gly Asn Lys Lys Val
1               5                   10

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Pro Ala Ile Asp Lys Ala Lys Gln Asp Val
1               5                   10

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide -continued (xi) SEQUENCE DESCRIPTION: SEQ ID NO:8:

Pro Ala Ile Asn Ser Asn Lys Gln Asp Val
1               5                   10

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CCTGCCATCA ACAAGGGCAA CAAGAAAGTC          30

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..30
        (D) OTHER INFORMATION: /note= "oligonucleotide probe
            mixture."

(xi) SEQUENCE DESCRIPTION: SEQ ID NO:10:

NCCTYCCACA ARGCCGCCTT CGGYATACAS          30

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Lys Lys Arg Cys Leu Trp
1               5